(12) United States Patent
Gunasekaran et al.

(10) Patent No.: US 9,063,073 B2
(45) Date of Patent: Jun. 23, 2015

(54) SOLID WORKING ELECTRODE WITH REPLACEABLE TIP

(71) Applicant: Wisconsin Alumni Research Foundation, Madison, WI (US)

(72) Inventors: Sundaram Gunasekaran, Madison, WI (US); Jiang Yang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 328 days.

(21) Appl. No.: 13/759,490

(22) Filed: Feb. 5, 2013

(65) Prior Publication Data

US 2013/0264202 A1 Oct. 10, 2013

Related U.S. Application Data

(60) Provisional application No. 61/620,257, filed on Apr. 4, 2012.

(51) Int. Cl.
*G01N 27/30* (2006.01)
*G01N 27/327* (2006.01)

(52) U.S. Cl.
CPC ......... *G01N 27/307* (2013.01); *Y10T 29/49117* (2015.01); *G01N 27/308* (2013.01); *G01N 27/3278* (2013.01)

(58) Field of Classification Search
CPC ............. Y10T 29/49117; G01N 27/30; G01N 27/307; G01N 27/308; G01N 27/3278
See application file for complete search history.

(56) References Cited

U.S. PATENT DOCUMENTS 4,882,029 A * 11/1989 Eickmann ..................... 204/400
5,531,743 A * 7/1996 Nettekoven et al. ............ 606/41
6,783,645 B2 8/2004 Cheng et al.

OTHER PUBLICATIONS

Ruby ("Metal Electrodes With Interchangeable Tips", Electroanal. Chem. and Interfacial Electrochem. 45, 1973, 141-148).*
P. Jandik, J. Cheng; Disposable Working Electrodes for HPLC Detection; PITTCON 2007 Presentation; pp. 1-4; Passion. Power. Productivity; Dionex; Sunnyvale, CA, USA.

* cited by examiner

*Primary Examiner* — Luan Van
*Assistant Examiner* — Steven Rosenwald
(74) *Attorney, Agent, or Firm* — Boyle Fredrickson, S.C.

(57) ABSTRACT

A working electrode for cyclic voltammetry experiments and the like provides an electrode carrier releasably attaching to replaceable tips each holding a solid working electrode material that may be polished for receipt of a reactant material and which electrically connects to an electrode in the electrode carrier when the tip and carrier are connected.

17 Claims, 2 Drawing Sheets

SOLID WORKING ELECTRODE WITH REPLACEABLE TIP

CROSS REFERENCE TO RELATED APPLICATION

This application claims the benefit of U.S. provisional application No. 61/620,257 filed Apr. 4, 2012 and hereby incorporated by reference.

STATEMENT REGARDING FEDERALLY SPONSORED RESEARCH OR DEVELOPMENT

This invention was made with government support under 11-CRHF-0-6055 awarded by the USDA/NIFA. The government has certain rights in the invention.

BACKGROUND OF THE INVENTION

The present invention relates to electrodes for electrochemical or related measurements, for example, HPLC-electrochemical, electrochemiluminescence, UV-electrochemistry, cyclic voltammetry measurements, and the like, and in particular to a solid-surface working electrode having replaceable tips.

The study of oxidation/reduction reactions in electrochemistry may use two or more solid surface electrodes in contact with an electrolyte. One electrode, termed a working electrode, may have a reactant applied to its surface whose interaction with the electrolyte is subject to the study. The reactant may be supported on a reactant substrate such as carbon nanotubes to enhance certain properties of the reactant materials by increasing the surface area, electrical conductivity, biocompatibility, reactant dispersion and the like.

The microstructure, cleanliness, and chemical composition of the working electrode surface greatly influence the measurement and use of the electrode. For frequently used glassy-carbon electrodes (GCE) or other kinds of metal electrodes, the surface to which the reactant or a reactant substrate is applied must be cleaned and may be pre-activated for use in a multi-step process. Such a process may include, for example, polishing the surface with a fine micro cloth and a successively finer 1.0, 0.3 and 0.05 $\mu m\alpha$-alumina slurry until a mirror-like surface is obtained. A mirror-like surface is one that provides substantially specular reflection in visible light frequencies.

The electrode is rinsed with double distilled water ($ddH_2O$) after each polishing. Sonication steps are performed consecutively in ethanol (or 1:1 $HNO_3$/ethanol, 0.5 M $H_2SO_4$, cyclohexane etc.) and $ddH_2O$, and the GCE is dried at room temperature (or by $N_2$ flow). In this typical cleaning process, high-quality double-distilled ultra pure "type 1" water (e.g. Milli-Q water) with resistivity greater than 18.2 M$\Omega$ must be used throughout the process, including rinsing, sonication, and making solutions. After this clean-up, an electrochemical scan (typically cyclic voltammetry) should be performed to confirm that the scan conforms to the characteristics of a 'fresh' electrode of the same kind.

Such treatments (polishing and sonication) expose fresh new surfaces of the electrode and remove old carbon particles and the remains of polishing materials. However, the cleaning conditions, such as sonication time and polishing pressure and time, are critical and polishing on some types of abrasive containing pads can result in deactivating the surface. Repeated sonications may eventually destroy the electrode by compromising the seal between the carbon and the outer cladding material, (e.g. Teflon) while the use of large particles (e.g. large size of alumina powder) for polishing can create unrepairable surface defects, scratches and indentations, making the electrodes become abraded and suffer poor performance, resulting in inaccurate measurements and loss of use of electrodes. These cleaning and polishing steps are also very time-consuming and laborious. Similar problems affect working electrodes formed of other materials.

SUMMARY OF THE INVENTION

The present invention provides a solid surface working electrode having replaceable tips. In this way the time-consuming surface preparation of the working electrode may be implemented on a mass production basis to reduce the time required for the laborious polishing process of individual electrode tips. The replaceable tips may be disposable to eliminate problems of damage and degradation of the working electrode surface after multiple polishings, as well as the need to run any electrochemical confirmation experiments.

Specifically then, the present invention provides a solid, working electrode for electrochemistry tests having an electrode carrier (or base) and multiple replaceable electrode tips. The electrode carrier provides an elongate insulating shaft having opposed first and second ends separated along a shaft axis and a carrier conductor passing between the first and second ends along the shaft axis through the insulating shaft to be surrounded in a direction radial to the axis by the insulating shaft, the electrode conductor exposed at the first and second ends for electrical connection thereto. The electrode tips each have a solid surface (which may or may not be modified with other entities such as nanoparticles, enzymes, or antibodies) working electrode conductor electrically connecting to the carrier conductor at the second end of the insulating shaft when the electrode tip is attached to the electrode carrier and an insulating material attached around at least a portion of the working electrode conductor to seal a connection between the working electrode conductor and the carrier conductor against liquid infusion when the electrode tip is attached to the electrode carrier. Attachment elements on the electrode tip and electrode carrier releasably retain the electrode carrier and electrode tip in attachment.

It is thus an object of at least one embodiment of the invention to simplify electrochemical measurements made with solid working electrodes by performing electrode preparation on a mass production basis to produce replaceable and disposable electrode tips at low cost.

The working electrode conductor may be any of gold, silver, platinum, graphite, and glassy carbon and pyrolytic carbon or any other carbon-based materials.

It is thus an object of at least one embodiment of the invention to provide a system that may provide common working electrode materials.

The working electrode conductor may have an axial thickness greater than 0.1 millimeters.

It is thus an object of at least one embodiment of the invention to provide a working electrode that may be polished and mechanically cleaned for high reproducibility in the results.

The exposed area of the working electrode conductor may be polished to a mirror surface It is thus an object of at least one embodiment of the invention to provide a surface superior to printed thin-film electrode surfaces.

The exposed planar area of the working electrode conductor may be greater than the area of the circle of diameter of substantially 1.6 millimeters and less than the area of a circle of diameter of substantially 3.0 millimeters.

It is thus an object of at least one embodiment of the invention to provide a working electrode having suitable area for typical cyclic voltammetry experiments.

The solid, working electrode may further include a reactant surface attached to an exposed area of the working electrode conductor at a location removed from the second end when the electrode tip is attached to the electrode carrier.

It is thus an object of at least one embodiment of the invention to permit pre-manufacture of working electrodes with particular reactant surfaces for common electrochemical experiments.

The reactant surface may include a reactant substrate of carbon nanotubes.

It is thus an object of at least one embodiment of the invention to provide a working electrode that may be pre-prepared with mechanically fragile substrate materials that require high temperature processing.

The attachment elements may be first and second magnets positioned on the electrode carrier and electrode tip respectively.

It is thus an object of at least one embodiment of the invention to provide a simple and intuitive attachment mechanism for the electrode tips.

The first magnet may be in electrical communication with the electrode conductor and attaches magnetically to the second magnet when the electrode tip is attached to the electrode carrier and the second magnet may be in electrical communication with the working electrode conductor.

It is thus an object of at least one embodiment of the invention to permit the magnets to provide for both mechanical and electrical interconnection of the tip and carrier.

The first and second magnets may connect to the electrode conductor and the working electrode conductor with conductive adhesive.

It is thus an object of at least one embodiment of the invention to provide a simple method of electrically connecting magnets to other conductors.

The attachment element on the electrode tip and electrode carrier may alternatively be inter-engaging mechanical snap elements.

It is thus an object of at least one embodiment of the invention to provide a low cost attachment method suitable for mass production.

The inter-engaging mechanical snap elements may be formed of insulating material of the electrode carrier and the electrode tip.

It is thus an object of at least one embodiment of the invention to employ the insulating materials both for electrical insulation and attachment.

The invention may provide a disposable electrode tip kit having an electrode carrier and multiple electrode tips in an electrode tip dispenser supporting the multiple electrode tips to expose first ends of the electrode tips attachable to the electrode carrier and to cover second ends of the electrode tips exposing areas of the working electrode conductor when the electrode tips are attached to the electric carrier.

It is thus an object of at least one embodiment of the invention to provide a convenient method of shipping and dispensing multiple electrode tips for easy use.

The electrode tip dispenser may support the electrode tips against axial movement from the first end to the second and by support elements displaced from exposed areas of the working electrode conductor.

It is thus an object of at least one embodiment of the invention to provide a dispenser that protects possibly fragile reactant surfaces from contamination and damage when engaged with the electrode carrier using axial pressure.

The invention may further provide a method of manufacturing the electrode tips in which a sheet of material of the working electrode conductor is prepared for electrochemical measurement and then the sheet is cut into multiple separate working electrode conductors. Each of the separate multiple working electrodes may then be attached to an attachment element releasably retaining an electrode carrier and the electrode tip in attachment and the insulating material may be applied around the portion of the working electrode conductor.

It is thus an object of the invention to improve the manufacturability of electrode tips by parallel processing of multiple working electrodes both in the polishing and cleaning and also in the attachment of reactant materials, particularly those that require high temperature or complex processing.

These particular objects and advantages may apply to only some embodiments falling within the claims and thus do not define the scope of the invention.

DETAILED DESCRIPTION OF THE PREFERRED EMBODIMENT

Figure 1:
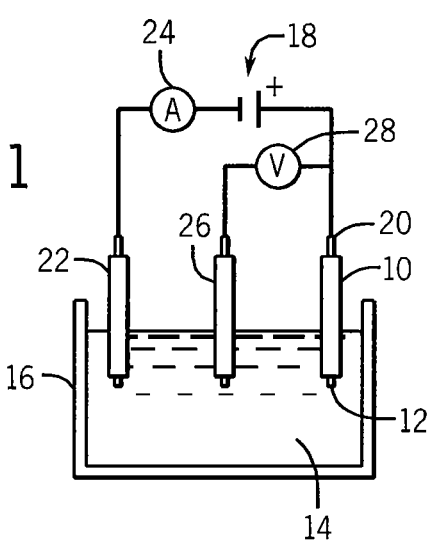
FIG. 1 is a simplified diagram of a typical experiment using a working electrode for cyclic voltammetry type experiments.
Figure 2:
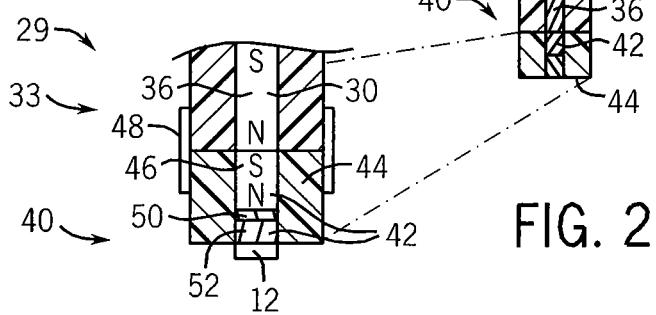
FIG. 2 is a partial cross-section of the working electrode in a first embodiment of the present invention also depicting an expanded fragmentary cross-section of the electrode showing an electrode carrier and a replaceable electrode tip using magnetic attachment elements.

Referring now to FIG. 1, a solid-surface working electrode 10 of the present invention may be used for electrochemical measurements in which a reactant surface 12 of the working electrode 10 is immersed in a liquid electrolyte 14, for example, held in an upwardly open container 16.

A voltage from a voltage source 18 may be applied across the working electrode 10, through an upper electrode terminal 20 and an auxiliary electrode 22, the latter also in electrical communication with the electrolyte 14. The current flowing between the two electrodes 10 and 22, through a circuit including the working electrode 10, the electrolyte 14, the auxiliary electrode 22, and the voltage source 18 may be measured with ammeter 24.

The voltage between the reactant surface 12 of the working electrode 10 and the electrolyte 14 may be determined using a separate reference electrode 26 also in communication with the electrolyte and communicating with the terminal 20 of the working electrode 10 through a voltmeter 28. The separate reference electrode 26 avoids errors caused by unknown resistances in the circuit.

This "three electrode" test set may be used, for example, for cyclic voltammetry or other similar experiments in which electrochemical properties are to be determined in the interaction between a reactant on the reactant surface 12 and the electrolyte 14.

The working electrode 10 may include an electrode carrier 29 having a central conductor 30, for example a copper rod passing coaxially along an axis 38 through an outer insulating sleeve 32. The outer insulating sleeve 32 may be, for example, Teflon®, formed to provide for a cylindrical annulus around the central conductor 30. The central conductor 30 may be press fit into the outer insulating sleeve 32 to seal therewith or may be sealed with an auxiliary material such as epoxy or the like.

At a first end 31 of the working electrode 10, the central conductor 30 may protrude to provide for the terminal 20. At a second end 33 of the electrode carrier 29, the central conductor 30 may be connected, via a thin conductive adhesive layer 34, with one end of a cylindrical permanent magnet 36 of comparable diameter, to the central conductor 30 and also aligned with the axis 38 of the conductor 30. The permanent magnet 36 is also held within the outer insulating sleeve 32 and sealed therein except for a circular base of the permanent magnet 36 removed from its interface with the central conductor 30, this circular base being exposed at the second end 33 of the electrode carrier 29. The permanent magnet 36 may be, for example, a conductive magnetic alloy such as Alnico or the like.

The second end 33 of the electrode carrier 29 releasably attaches to a replaceable electrode tip 40, for example, having a similar diameter to the electrode carrier 29 and extending from the second end 33 along axis 38. The electrode tip 40 provides a central conductor 42 surrounded by an insulating sleeve 44, for example, Teflon®, forming a protective cylindrical annulus around the conductor 42. In this embodiment, a portion of the conductor 42 closest to the electrode carrier 29 may be formed of a second permanent magnet 46 having a polarity so as to attract it to the permanent magnet 36 of the electric carrier 29 and to generally align the conductor 42 with the conductor 30 along axis 38. Electricity may be conducted through the interface between the magnets 46 and 36 from the central conductor 30 to the central conductor 42.

When the magnets 46 and 36 are attached end-to-end, the insulating sleeves 32 and 44 closely abut to seal the interface between the magnets 46 and 36 against the infusion of electrolyte 14 such as might create a separate reaction site. Such sealing as may be augmented by a surrounding annular sleeve 48 of additional insulation material, for example, may be formed of an application of a two-part epoxy applied thereabout or other similar sealing material including an elastomeric material or an extension of the insulating sleeve 44.

Within the electrode tip 40, the end of the magnet 36 removed from the point of attachment to the electric carrier 29 may be attached by a thin conductive adhesive 50 (such as a silver impregnated epoxy or the like) to a solid working electrode material 52. The solid working electrode material 52 may have axial length of greater than 0.1 mm and sufficient so that it may be mechanically polished to a mirror-like smoothness and so that it is self-supporting without attachment to the magnet 46 or insulating sleeve 44 for polishing and processing with reactant substrates and materials as will be described below. The solid working electrode material 52 may be, for example, selected from the group consisting of: gold, silver, platinum, and carbon, wherein the carbon may be glassy carbon or pyrolytic carbon or graphite which is inexpensive.

An opposed end of the solid working electrode material 52, removed from its point of attachment to magnet 46, may be exposed through the insulating sleeve 44 to provide a reaction surface that, as noted, may be polished to the mirror-like smoothness. A reactant surface 12, being either a reactant subject to the electrochemical reaction of the desired experiment, or a reactant substrate such as carbon nanotubes, may be attached to this exposed portion of the solid working electrode material 52.

When the electrode tip 40 is assembled to the electrode carrier 29 and properly sealed by the close abutment of the insulating sleeves 44 and 32 augmented possibly with the sleeve 48, the second end 33 of the electrode carrier 29 may be immersed in the electrolyte 14 for measurement of desired electrical properties of the reactant of the reactant surface 12.

Figure 3:
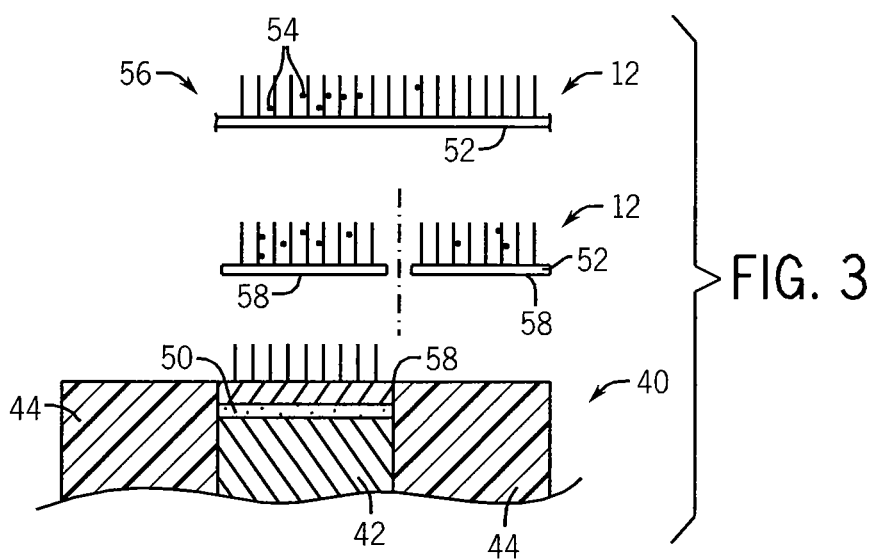
FIG. 3 is a simplified process diagram of the steps of fabrication of the electrode tip of FIG. 2.

Referring now to FIG. 3, electrode tips 40 may be mass-produced to eliminate the time-consuming polishing and cleaning of the working electrode tip on an electrode-by-electrode basis as required in the prior art. In one such fabrication technique, solid working electrode material 52 in the form of a plate 56 may be treated to apply the reactant surface 12, in this case a substrate of carbon nanotubes, to one surface. Carbon nanotubes may be grown on the solid working electrode material 52 using a high temperature process generally understood in the art and that would be damaging to most polymeric insulating materials or thin substrates. Prior to this growth, the surface of the solid working electrode material 52 may be polished and cleaned appropriately. Optionally, a reactant 54 may then be applied to the reactant surface 12. The reactant 54 may include, for example, enzyme-labeled materials or the like. Reactants 54 may also be attached directly to the plate 56 by a number of processes including electrode deposition, magnetron sputtering, spin coating, direct casting, or the like. Alternatively, the solid working electrode material 52 of plate 56 may be cleaned and polished with or without further coating.

The plate 56 may then be divided into individual die 58, for example, by punching or shearing the plate 56 into portions having an area comparable to the area of the disk 1.6 to 3 millimeters in diameter. This separation process preferably minimizes any damage to the reactant surface 12. Each of the separated dies 58 may then be attached to the conductors 42 of the electrode tips 40 with the adhesive 50 and shrouded by the insulating sleeve 44 to provide one tip 40. The ability to simultaneously treat the surface of multiple dies 58 in a plate 56 form greatly simplifies the steps of manufacturing the tips 40.

Figure 5:
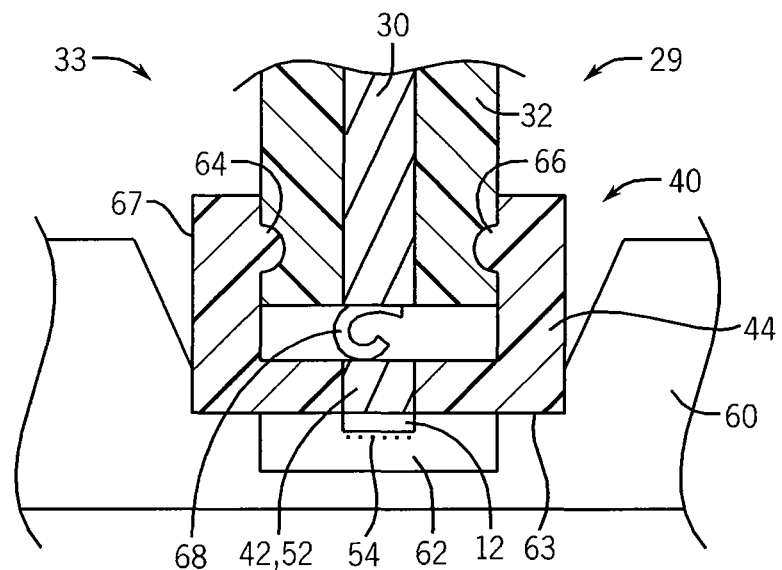
FIG. 5 is a figure similar to the expanded fragment of FIG. 2 showing alternative mechanical attachment elements.

Referring now to FIG. 5, in an alternative embodiment, the tip 40 may be attached to the carrier 29 by a mechanical attachment mechanism, for example, a snap fitting providing on the electrode carrier 29 an annular groove 64 passing circumferentially around the second end 33 of the carrier 29. This annular groove 64 may receive a corresponding ridge 66 extending radially inwardly from the inner surface of an annular lip 67 extending upwardly from the insulating sleeve 44 of the tip 40. This annular lip 67 may have an inner diameter approximating the outer diameter of the insulating sleeve 32 so that the annular ridge 66 may pass over a lower edge of the insulating sleeve 32 taking advantage of small scale elasticity of the polymeric material from which is constructed to then be received within the annular groove 64 in a tight and water resistance seal. This seal may be augmented and the engagement between the electric carrier 29 and the tip 40 promoted by a thin layer of silicon grease or the like precharged into the space within the annular lip 67. A conductive flexible spring 68 or similar mechanism may be attached to a lowermost end of the conductor 30 (in this embodiment of omitting the magnet 36) to directly connect with the conductor 42 (also omitting the magnet) held coaxially within the insulating sleeve 44 as before.

Figure 4:
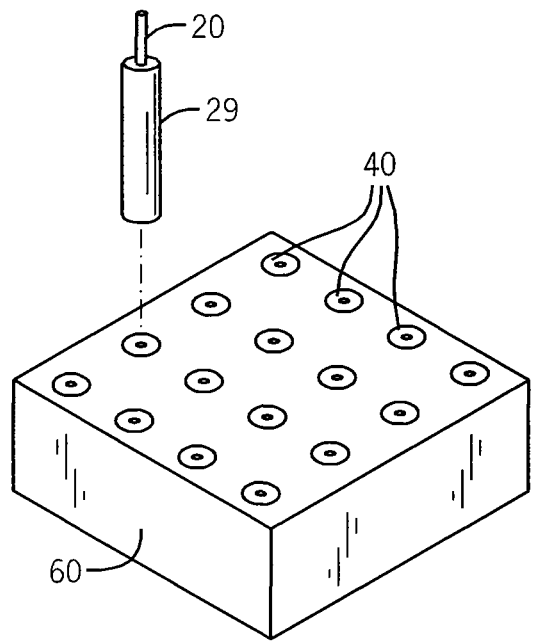
FIG. 4 is a perspective view of a carrier holding multiple electrode tips for attachment to an electrode carrier.

Referring now to FIG. 4, multiple tips 40 may be placed in a dispenser 60 presenting an upwardly accessible face having multiple openings into which the tips 40 may be placed with the magnets 46 or annular lips 67 of each tip 40 oriented upward. In this way, and electrode carrier 29 may simply be lowered over one of the openings in the dispenser 60 and attached to a given tip 40 from that carrier 29 without the need to handle the tips 40 or perform cleaning or other processing steps.

Referring again also to FIG. 5, the dispenser 60 may include a pocket 62 beneath the reactant surface 12 to protected the latter from abrasion during shipping and the force of engagement of the carrier 29 with the tip 40, the force being borne by circumferential ledges 63 engaging corresponding outer peripheral lower ledges of the insulating sleeve 44. The dispenser 60 may be injection molded thermoplastic material or the like.

Generally, the electrode carrier 29 will be relatively stiff and inflexible to simplify the engagement process.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

The invention claimed is:

1. A solid, working electrode for electrochemistry tests comprising:
an electrode carrier having:
 (a) an elongate insulating shaft having opposed first and second ends separated along a shaft axis;
 (b) a carrier conductor passing between the first and second ends along the shaft axis through the insulating shaft to be surrounded in a direction radial to the axis by the insulating shaft, the electrode conductor exposed at the first and second ends for electrical connection thereto; and
an electrode tip releasably attachable to the electrode carrier, the electrode tip having:
 (a) a solid surface working electrode conductor electrically connecting to the carrier conductor at the second end of the insulating shaft when the electrode tip is attached to the electrode carrier;
 (b) an insulating material attached around at least a portion of the working electrode conductor to seal a connection between the working electrode conductor and the carrier conductor against liquid infusion when the electrode tip is attached to the electrode carrier; and
 (c) attachment elements on the electrode tip and electrode carrier releasably retaining the electrode carrier and electrode tip in attachment;
wherein the attachment elements are first and second magnets positioned on the electrode carrier and electrode tip respectively.

2. The solid, working electrode of claim 1 wherein the working electrode conductor is selected from the group consisting of: gold, silver, platinum, and carbon.

3. The solid, working electrode of claim 2 wherein the carbon is selected from the group consisting of glassy carbon and pyrolytic carbon.

4. The solid, working electrode of claim 1 wherein the working electrode conductor has an axial thickness greater than 0.1 millimeters.

5. The solid, working electrode of claim 4 wherein an exposed area of the working electrode conductor at a location removed from the second end when the electrode tip is attached to the electrode carrier is polished to a mirror surface.

6. The solid, working electrode of claim 1 wherein an exposed planar area of the working electrode conductor is greater than the area of a circle of diameter of substantially 1 millimeter.

7. The solid, working electrode of claim 1 wherein an exposed planar area of the working electrode conductor is less than the area of a circle of diameter of substantially 4 millimeters.

8. The solid, working electrode of claim 1 wherein an exposed planar area of the working electrode conductor is greater than the area of a circle of diameter of substantially 1.6 millimeters and less than the area of a circle of diameter of substantially 3.0 millimeters.

9. The solid, working electrode of claim 1 further including:
a reactant surface attached to an exposed area of the working electrode conductor at a location removed from the second end when the electrode tip is attached to the electrode carrier.

10. The solid, working electrode of claim 9 wherein the reactant surface includes a reactant substrate of carbon nanotubes.

11. The solid, working electrode of claim 1 wherein the first magnet is in electrical communication with the electrode conductor and attaches magnetically to the second magnet when the electrode tip is attached to the electrode carrier and the second magnet is in electrical communication with the working electrode conductor.

12. The solid, working electrode of claim 1 wherein the first and second magnets connect to the electrode conductor and the working electrode conductor with conductive adhesive.

13. A disposable electrode tip kit comprising:
an electrode carrier having:
 (a) an elongate insulating shaft having opposed first and second ends separated along a shaft axis;
 (b) a carrier conductor passing between the first and second ends along the shaft axis through the insulating shaft to be surrounded in a direction radial to the axis by the insulating shaft, the electrode conductor exposed at the first and second ends for electrical connection thereto; and an electrode tip dispenser holding multiple electrode tips releasably attachable to the electrode carrier, the electrode tips having:
(a) a solid surface working electrode conductor electrically connecting to the carrier conductor at the second end of the insulating shaft when the electrode tip is attached to the electrode carrier;
(b) an insulating material attached around at least a portion of the working electrode conductor to seal a connection between the working electrode conductor and the carrier conductor against liquid infusion when the electrode tip is attached to the electrode carrier; and
(c) attachment elements on the electrode tip and electrode carrier releasably retaining the electrode carrier and electrode tip in attachment;
wherein the electrode tip dispenser supports the multiple electrode tips to expose first ends of the electrode tips attachable to the electrode carrier and to cover second ends of the electrode tips exposing areas of the working electrode conductor when the electrode tips are attached to the electrode carrier;
wherein the attachment elements are first and second magnets positioned on the electrode carrier and electrode tip respectively.

14. The disposable electrode tip kit of claim 13 wherein the electrode tip dispenser supports the electrode tips against axial movement from the first end to the second and by support elements displaced from exposed areas of the working electrode conductor.

15. The disposable electrode tip kit of claim 14 wherein the electrode tips further include a reactant surface attached to an exposed area of the working electrode conductor at a location removed from the second end when the electrode tip is attached to the electrode carrier and wherein the reactant surface includes a reactant substrate of carbon nanotubes.

16. A method of manufacturing electrode tips for use with an electrode carrier having an elongate insulating shaft having opposed first and second ends separated along a shaft axis and a carrier conductor passing between the first and second ends along the shaft axis through the insulating shaft to be surrounded in a direction radial to the axis by the insulating shaft, the electrode conductor exposed at the first and second ends for electrical connection thereto, the electrode tips each having a solid surface working electrode conductor electrically connecting to the carrier conductor at the second end of the insulating shaft when the electrode tip is attached to the electrode carrier; an insulating material attached around at least a portion of the working electrode conductor to seal a connection between the working electrode conductor and the carrier conductor against liquid infusion when the electrode tip is attached to the electrode carrier; and attachment elements on the electrode tip and electrode carrier releasably retaining the electrode carrier and electrode tip in attachment, wherein the attachment elements are first and second magnets positioned on the electrode carrier and electrode tip respectively, comprising the steps of:
(a) preparing a sheet of material of the working electrode conductor for electrochemical measurement;
(b) cutting the sheet into multiple separate working electrode conductors;
(c) attaching each of the separate multiple working electrodes to a magnet providing an attachment element releasably retaining an electrode carrier and the electrode tip in attachment; and
(d) applying the insulating material around the portion of the working electrode conductor.

17. The method of claim 16 wherein the step of preparing the sheet of material of the working electrode includes applying a reactant surface to the sheet wherein the reactant surface includes a reactant substrate of carbon nanotubes.

* * * * *